(12) United States Patent
Dumbauld et al.

(10) Patent No.: US 8,968,305 B2
(45) Date of Patent: Mar. 3, 2015

(54) SURGICAL FORCEPS WITH EXTERNAL CUTTER

(75) Inventors: Patrick L. Dumbauld, Lyons, CO (US); Glenn A. Horner, Boulder, CO (US); Duane E. Kerr, Loveland, CO (US); Kathy E. Rooks, Aurora, CO (US); Jessica E. C. Olson, Frederick, CO (US)

(73) Assignee: Covidien LP, Mansfield, MA (US)

( * ) Notice: Subject to any disclaimer, the term of this patent is extended or adjusted under 35 U.S.C. 154(b) by 984 days.

(21) Appl. No.: 13/072,945

(22) Filed: Mar. 28, 2011

(65) Prior Publication Data

US 2012/0253344 A1 Oct. 4, 2012

(51) Int. Cl.
| | |
|---|---|
| *A61B 18/12* | (2006.01) |
| *A61B 18/14* | (2006.01) |
| *A61B 17/29* | (2006.01) |
| *A61B 18/00* | (2006.01) |
| *A61B 17/3209* | (2006.01) |

(52) U.S. Cl.
CPC ............. *A61B 18/1445* (2013.01); *A61B 17/29* (2013.01); *A61B 2018/00196* (2013.01); *A61B 2018/00601* (2013.01); *A61B 2018/0063* (2013.01); *A61B 2018/1452* (2013.01); *A61B 17/3209* (2013.01); *A61B 2017/2926* (2013.01)
USPC ............................................. 606/51; 606/52

(58) Field of Classification Search
CPC .................. A61B 18/1445; A61B 2018/1455; A61B 2018/0063; A61B 2018/00595; A61B 17/282; A61B 2018/00601; A61B 18/085; A61B 18/1442; A61B 18/1447
See application file for complete search history.

(56) References Cited

U.S. PATENT DOCUMENTS

| | | | |
|---|---|---|---|
| D249,549 | S | 9/1978 | Pike |
| D263,020 | S | 2/1982 | Rau, III |
| D295,893 | S | 5/1988 | Sharkany et al. |
| D295,894 | S | 5/1988 | Sharkany et al. |
| D298,353 | S | 11/1988 | Manno |
| D299,413 | S | 1/1989 | DeCarolis |
| D343,453 | S | 1/1994 | Noda |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

U.S. Appl. No. 08/926,869, filed Sep. 10, 1997, James G. Chandler, Copy attached.

(Continued)

*Primary Examiner* — Michael Peffley
*Assistant Examiner* — Daniel Fowler

(57) ABSTRACT

A forceps includes an end effector assembly defining a longitudinal axis and including a pair of jaw members disposed in opposing relation relative to one another. At least one jaw member is moveable relative to the other between a spaced-apart position and an approximated position for grasping tissue therebetween. Each jaw member includes a jaw housing and an opposed electrically conductive sealing surface. The opposed sealing surfaces define a sealing area therebetween. A cutting mechanism is disposed on the jaw housing of one of the jaw members opposite the respective sealing surface and is configured to cut tissue externally-positioned relative to the sealing area upon translation of the cutting mechanism with respect to tissue.

5 Claims, 3 Drawing Sheets

(56) References Cited

U.S. PATENT DOCUMENTS

| | | |
|---|---|---|
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,445,638 A | 8/1995 | Rydell et al. |
| D384,413 S | 9/1997 | Zlock et al. |
| 5,797,927 A | 8/1998 | Yoon |
| D402,028 S | 12/1998 | Grimm et al. |
| D416,089 S | 11/1999 | Barton et al. |
| D424,694 S | 5/2000 | Tetzlaff et al. |
| D425,201 S | 5/2000 | Tetzlaff et al. |
| D449,886 S | 10/2001 | Tetzlaff et al. |
| D454,951 S | 3/2002 | Bon |
| D457,958 S | 5/2002 | Dycus et al. |
| D457,959 S | 5/2002 | Tetzlaff et al. |
| D465,281 S | 11/2002 | Lang |
| D466,209 S | 11/2002 | Bon |
| 6,527,771 B1 | 3/2003 | Weadock et al. |
| D493,888 S | 8/2004 | Reschke |
| 6,790,217 B2 * | 9/2004 | Schulze et al. ............ 606/171 |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| 7,063,699 B2 | 6/2006 | Hess et al. |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| 7,147,637 B2 * | 12/2006 | Goble ............................ 606/50 |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| 7,367,976 B2 | 5/2008 | Lawes et al. |
| D575,395 S | 8/2008 | Hushka |
| D575,401 S | 8/2008 | Hixson et al. |
| D582,038 S | 12/2008 | Swoyer et al. |
| 7,481,810 B2 | 1/2009 | Dumbauld et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,776,036 B2 * | 8/2010 | Schechter et al. ............ 606/51 |
| D627,462 S | 11/2010 | Kingsley |
| D628,289 S | 11/2010 | Romero |
| D628,290 S | 11/2010 | Romero |
| 7,846,161 B2 | 12/2010 | Dumbauld et al. |
| D630,324 S | 1/2011 | Reschke |
| 2003/0195513 A1 * | 10/2003 | Truckai et al. ............... 606/51 |
| 2004/0049185 A1 * | 3/2004 | Latterell et al. ............. 606/48 |
| 2004/0122423 A1 * | 6/2004 | Dycus et al. .................. 606/51 |
| 2004/0254573 A1 * | 12/2004 | Dycus et al. .................. 606/51 |
| 2005/0004570 A1 * | 1/2005 | Chapman et al. ............ 606/51 |
| 2005/0149017 A1 * | 7/2005 | Dycus ........................... 606/51 |
| 2005/0256522 A1 * | 11/2005 | Francischelli et al. ........ 606/41 |
| 2006/0020265 A1 * | 1/2006 | Ryan ............................ 606/48 |
| 2006/0116675 A1 * | 6/2006 | McClurken et al. ........... 606/51 |
| 2006/0129146 A1 * | 6/2006 | Dycus et al. .................. 606/51 |
| 2006/0173452 A1 * | 8/2006 | Buysse et al. ................. 606/50 |
| 2006/0224158 A1 * | 10/2006 | Odom et al. .................. 606/51 |
| 2006/0293656 A1 * | 12/2006 | Shadduck et al. ............ 606/51 |
| 2007/0055231 A1 * | 3/2007 | Dycus et al. .................. 606/51 |
| 2007/0142833 A1 * | 6/2007 | Dycus et al. .................. 606/51 |
| 2007/0179499 A1 * | 8/2007 | Garrison ....................... 606/51 |
| 2008/0021450 A1 * | 1/2008 | Couture ........................ 606/51 |
| 2008/0039836 A1 * | 2/2008 | Odom et al. .................. 606/51 |
| 2008/0114356 A1 * | 5/2008 | Johnson et al. ............... 606/51 |
| 2008/0243120 A1 * | 10/2008 | Lawes et al. .................. 606/51 |
| 2009/0131933 A1 * | 5/2009 | Ghabrial et al. .............. 606/51 |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 19738457 | 1/2009 |
| DE | 10 2008 018406 | 7/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 6-285078 | 10/1994 |
| JP | 6-511401 | 12/1994 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| JP | 2001-190564 | 7/2001 |
| SU | 401367 | 11/1974 |
| WO | WO 00/36986 | 6/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/576,380, filed Oct. 9, 2009, Wayne Siebrecht.
U.S. Appl. No. 12/607,191, filed Oct. 28, 2009, William H. Nau Jr.
U.S. Appl. No. 12/619,100, filed Nov. 16, 2009, Jennifer S. Harper.
U.S. Appl. No. 12/692,414, filed Jan. 22, 2010, Peter M. Mueller.
U.S. Appl. No. 12/696,592, filed Jan. 29, 2010, Jennifer S. Harper.
U.S. Appl. No. 12/696,857, filed Jan. 29, 2010, Edward M. Chojin.
U.S. Appl. No. 12/700,856, filed Feb. 5, 2010, James E. Krapohl.
U.S. Appl. No. 12/719,407, filed Mar. 8, 2010, Arlen J. Reschke.
U.S. Appl. No. 12/728,994, filed Mar. 22, 2010, Edward M. Chojin.
U.S. Appl. No. 12/748,028, filed Mar. 26, 2010, Jessica E.C. Olson.
U.S. Appl. No. 12/757,340, filed Apr. 9, 2010, Carine Hoarau.
U.S. Appl. No. 12/758,524, filed Apr. 12, 2010, Duane E. Kerr.
U.S. Appl. No. 12/759,551, filed Apr. 13, 2010, Glenn A. Horner.
U.S. Appl. No. 12/769,444, filed Apr. 28, 2010, Glenn A. Norner.
U.S. Appl. No. 12/770,369, filed Apr. 29, 2010, Glenn A. Horner.
U.S. Appl. No. 12/770,380, filed Apr. 29, 2010, Glenn A. Horner.
U.S. Appl. No. 12/770,387, filed Apr. 29, 2010, Glenn A. Horner.
U.S. Appl. No. 12/773,526, filed May 4, 2010, Duane E. Kerr.

(56) References Cited

OTHER PUBLICATIONS

U.S. Appl. No. 12/773,644, filed May 4, 2010, Thomas J. Gerhardt.
U.S. Appl. No. 12/786,589, filed May 25, 2010, Duane E. Kerr.
U.S. Appl. No. 12/791,112, filed Jun. 1, 2010, David M. Garrison.
U.S. Appl. No. 12/792,001, filed Jun. 2, 2010, Duane E. Kerr.
U.S. Appl. No. 12/792,008, filed Jun. 2, 2010, Duane E. Kerr.
U.S. Appl. No. 12/792,019, filed Jun. 2, 2010, Duane E. Kerr.
U.S. Appl. No. 12/792,038, filed Jun. 2, 2010, Glenn A. Horner.
U.S. Appl. No. 12/792,051, filed Jun. 2, 2010, David M. Garrison.
U.S. Appl. No. 12/792,068, filed Jun. 2, 2010, Glenn A. Horner.
U.S. Appl. No. 12/792,097, filed Jun. 2, 2010, Duane E. Kerr.
U.S. Appl. No. 12/792,262, filed Jun. 2, 2010, Jeffrey M. Roy.
U.S. Appl. No. 12/792,299, filed Jun. 2, 2010, Jeffrey M. Roy.
U.S. Appl. No. 12/792,330, filed Jun. 2, 2010, David M. Garrison.
U.S. Appl. No. 12/822,024, filed Jun. 23, 2010, Peter M. Mueller.
U.S. Appl. No. 12/821,253, filed Jun. 23, 2010, Edward M. Chojin.
U.S. Appl. No. 12/832,772, filed Jul. 8, 2010, Gary M. Couture.
U.S. Appl. No. 12/843,384, filed Jul. 26, 2010, David M. Garrison.
U.S. Appl. No. 12/845,203, filed Jul. 28, 2010, Gary M. Couture.
U.S. Appl. No. 12/853,896, filed Aug. 10, 2010, William H. Nau, Jr.
U.S. Appl. No. 12/859,896, filed Aug. 20, 2010, Peter M. Mueller.
U.S. Appl. No. 12/861,198, filed Aug. 23, 2010, James A. Gilbert.
U.S. Appl. No. 12/861,209, filed Aug. 23, 2010, William H. Nau, Jr.
U.S. Appl. No. 12/876,668, filed Sep. 7, 2010, Sara E. Anderson.
U.S. Appl. No. 12/876,680, filed Sep. 7, 2010, Peter M. Mueller.
U.S. Appl. No. 12/876,705, filed Sep. 7, 2010, Kristin D. Johnson.
U.S. Appl. No. 12/876,731, filed Sep. 7, 2010, Kristin D. Johnson.
U.S. Appl. No. 12/877,199, filed Sep. 8, 2010, Arlen J. Reschke.
U.S. Appl. No. 12/877,482, filed Sep. 8, 2010, Gary M. Couture.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/004,984, filed Jan. 12, 2011, David M. Garrison.
U.S. Appl. No. 13/006,538, filed Jan. 14, 2011, John W. Twomey.
U.S. Appl. No. 13/029,390, filed Feb. 17, 2011, Michael C. Moses.
U.S. Appl. No. 13/030,231, filed Feb. 18, 2011, Jeffrey M. Roy.
U.S. Appl. No. 13/048,679, filed Mar. 15, 2011, Paul Guerra.
U.S. Appl. No. 13/075,847, filed Mar. 30, 2011, Gary M. Couture.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectomy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.

(56) References Cited

OTHER PUBLICATIONS

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181969.6 dated Feb. 4, 2011.
Int'l Search Report EP 10 191320.0 dated Feb. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.

(56) References Cited

OTHER PUBLICATIONS

Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

SURGICAL FORCEPS WITH EXTERNAL CUTTER

BACKGROUND

The present disclosure relates to surgical instruments. More particularly, the present disclosure relates to surgical forceps including external cutting mechanisms for sealing and/or cutting tissue.

TECHNICAL FIELD

Electrosurgical forceps utilize both mechanical clamping action and electrical energy to effect hemostasis by heating tissue and blood vessels to coagulate, cauterize and/or seal tissue. As an alternative to open forceps for use with open surgical procedures, many modern surgeons use endoscopic or laparoscopic instruments for remotely accessing organs through smaller, puncture-like incisions or natural orifices. As a direct result thereof, patients tend to benefit from less scarring and reduced healing time.

Endoscopic instruments, for example, are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue. Typically, after a vessel or tissue is sealed, the surgeon advances a knife to sever the sealed tissue disposed between the opposing jaw members.

SUMMARY

The present disclosure relates to a surgical instrument, e.g., a forceps, including an end effector assembly defining a longitudinal axis. The end effector assembly includes a pair of jaw members disposed in opposing relation relative to one another. One or both jaw members are moveable relative to each other between a spaced-apart position and an approximated position for grasping tissue therebetween. Each jaw member includes a jaw housing and an opposed electrically conductive sealing surface. The opposed sealing surfaces define a sealing area therebetween. A cutting mechanism is disposed on the jaw housing of one of the jaw members opposite the respective sealing surface. The cutting mechanism is configured to cut tissue externally-positioned relative to the sealing area upon translation of the cutting mechanism with respect to tissue.

In one embodiment, the cutting mechanism includes a longitudinally extending blade track having a distal end and a proximal end. A cutting blade is engaged within and longitudinally translatable with respect to the blade track. Upon actuation, the cutting blade is translated proximally along the blade track to cut tissue disposed within the cutting mechanism.

In another embodiment, the cutting blade is biased toward the distal end of the blade track. The distal end of the blade track may be nested within a blade protector such that the cutting blade is disposed within the blade protector when the cutting blade is positioned at the distal end of the blade track.

In another embodiment, a stop member is positioned at the proximal end of the blade track.

In yet another embodiment, the cutting mechanism includes a cutting blade having a proximally-facing cutting edge extending from the jaw housing. The cutting blade is thus positioned to cut tissue upon distal translation of the end effector assembly with respect to tissue.

Alternatively, the cutting mechanism may include a cutting blade extending from and oriented proximally with respect to the jaw housing. In such an embodiment, the cutting blade is positioned to cut tissue upon proximal translation of the end effector assembly with respect to tissue. The cutting mechanism may further include a blade holder positioned distally of the cutting blade and configured to prevent the cutting blade from cutting tissue when the end effector assembly is translated distally with respect to tissue.

In still another embodiment, the cutting blade is moveable between an unexposed position, wherein the cutting blade is disposed within the jaw housing, and an exposed position, wherein the cutting blade extends from the jaw housing for cutting tissue.

In another embodiment, the cutting mechanism includes a dissecting electrode extending from the jaw housing and configured to conduct electrosurgical energy through tissue to electrically cut tissue upon movement of the end effector assembly in a direction normal to the longitudinal axis. The dissecting electrode may be a monopolar electrode or a bipolar electrode.

In accordance with another embodiment of the present disclosure, a surgical instrument is provided. The surgical instrument includes an end effector assembly having a pair of jaw members disposed in opposing relation relative to one another. One (or both) of the jaw members is moveable relative to the other between a spaced-apart position and an approximated position for grasping tissue therebetween. Each jaw member includes a jaw housing and an opposed electrically conductive sealing surface. The opposed sealing surfaces define a sealing area therebetween. A cutting mechanism is disposed on an external periphery of the jaw housing of one of the jaw members opposite the sealing area. The cutting mechanism includes a blade track extending longitudinally therealong. A cutting blade is engaged within the blade track and is longitudinally translatable with respect to the blade track between a distal end and a proximal end thereof to cut tissue disposed therebetween.

In accordance with yet another embodiment of the present disclosure, a surgical instrument is provided. The surgical instrument includes an end effector assembly defining a longitudinal axis and including a pair of jaw members disposed in opposing relation relative to one another. The jaw member(s) are moveable relative to each other between a spaced-apart position and an approximated position for grasping tissue therebetween. Each jaw member includes a jaw housing having an external top surface, a distal tip and an opposed electrically conductive sealing surface adapted to connect to a source of electrosurgical energy for sealing tissue disposed therebetween. A dissecting electrode extends from the external top surface of the jaw housing of one of the jaw members in a direction normal to the longitudinal axis. The dissecting electrode is adapted to connect to a source of electrosurgical energy to electrically cut tissue upon translation of the dissecting electrode with respect to tissue.

BRIEF DESCRIPTION OF THE DRAWINGS

Various embodiments of the presently disclosed surgical instruments are described herein with reference to the drawings, wherein.

DETAILED DESCRIPTION

Figure 1:
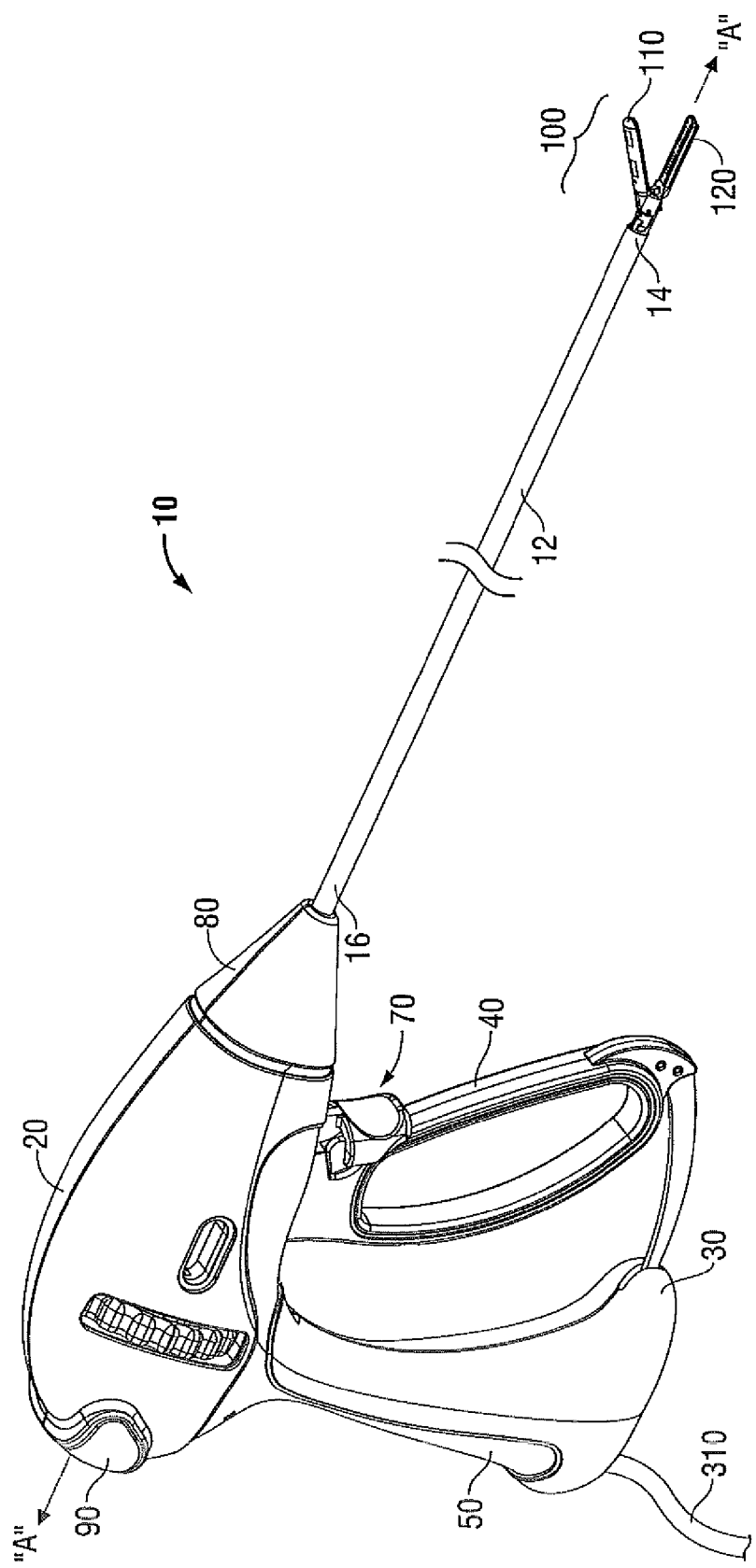
FIG. 1 is a perspective view of a forceps having an end effector assembly in accordance with an embodiment of the present disclosure.

Embodiments of the presently disclosed surgical instrument are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Turning now to FIG. 1, a forceps 10 is provided including a housing 20, a handle assembly 30, a rotating assembly 80, a trigger assembly 70 and an end effector assembly 100. Forceps 10 further includes a shaft 12 having a distal end 14 configured to mechanically engage end effector assembly 100 and a proximal end 16 that mechanically engages housing 20. Forceps 10 also includes electrosurgical cable 310 that connects forceps 10 to a generator (not shown), although forceps 10 may alternatively be configured as a battery powered device. Cable 310 has sufficient length to extend through shaft 12 in order to provide electrical energy to at least one of jaw members 110 and 120 of end effector assembly 100.

With continued reference to FIG. 1, handle assembly 30 includes fixed handle 50 and a moveable handle 40. Fixed handle 50 is integrally associated with housing 20 and handle 40 is moveable relative to fixed handle 50. Rotating assembly 80 is integrally associated with housing 20 and is rotatable in either direction about a longitudinal axis "A." The housing 20 includes two halves that house the internal working components of the forceps 10.

Although an endoscopic instrument is utilized in the figures and description to illustrate principles of the present invention, an open surgical instrument is also contemplated. For example, a hemostat-style instrument or scissors-type open surgical instrument may be applicable to the present invention.

Figure 2:
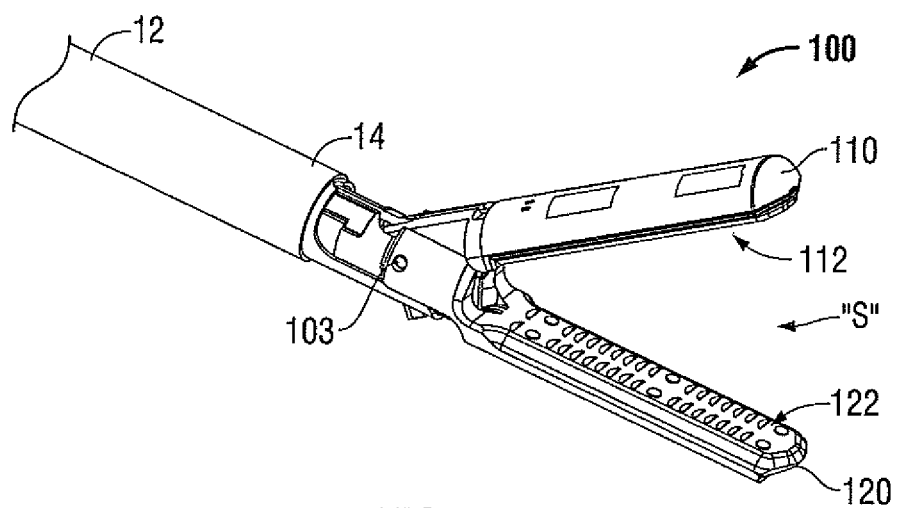
FIG. 2 is an enlarged perspective view of the end effector assembly of the forceps of FIG. 1.

Turning now to FIG. 2, end effector assembly 100 is shown attached at a distal end 14 of shaft 12 and includes a pair of opposing jaw members 110 and 120. Each of jaw members 110 and 120 includes an electrically conductive tissue sealing surface 112 and 122, respectively, that is configured to oppose the other, as shown in FIG. 2. Sealing surfaces 112, 122 define a sealing area "S" therebetween. End effector assembly 100 is designed as a unilateral assembly, i.e. jaw member 120 is fixed relative to the shaft 12 and jaw member 110 is moveable about a pivot 103 relative to jaw member 120. However, either, or both jaw members 110, 120 may be moveable with respect to the other.

As shown in FIG. 2, sealing surfaces 112, 122 extend completely across the opposing surfaces of jaw members 110, 120, respectively, i.e., a channel need not be defined within sealing surfaces 112, 122, for example, to accommodate translation of a knife therethrough. As will be described below, the externally mounted cutting mechanisms (see FIGS. 3-6) of the present disclosure obviate the need to translate a blade through jaw members 110, 120 to cut tissue. However, knife channels (not shown) may be defined within sealing surfaces 112, 122 such that a knife may be translated through jaw members 110, 120 to cut tissue disposed therebetween. Accordingly, in such an embodiment, the end effector assembly would include both an internal cutting mechanism for cutting tissue disposed between jaw members 110, 120, and an external cutting mechanism (See FIGS. 3-6) for cutting tissue external of jaw members 110, 120.

Various embodiments of end effector assemblies configured for use with surgical forceps 10 are described in detail with reference to FIGS. 3-6. More particularly, each pair of jaw members includes a cutting mechanism disposed externally on one of the jaw members. The end effector assemblies described below are configured for dissecting tissue to reach a desired surgical site, e.g., a vessel to be sealed, sealing tissue, and/or cutting previously sealed tissue. Thus, a single surgical instrument, e.g., forceps 10, is provided for dissecting tissue, sealing tissue and cutting sealed tissue.

Figure 3:
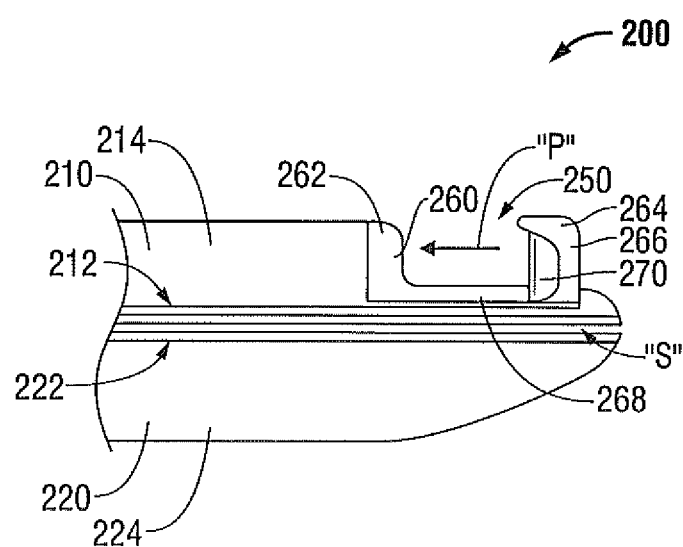
FIG. 3 is a side view of one embodiment of an end effector assembly for use with the forceps of FIG. 1.

With reference now to FIG. 3, end effector assembly 200 includes a pair of jaw members 210, 220 each including a respective tissue sealing surface 212, 222 and a jaw housing 214, 224, respectively. Jaw members 210, 220 are moveable with respect to each other between a spaced-apart position and an approximated position for grasping tissue therebetween. With tissue grasped between jaw member 210, 220, and more particularly, between sealing surfaces 212, 222, electrosurgical energy may be conducted to sealing surfaces 212, 222 and through tissue disposed within the sealing area "S" to effect a tissue seal.

With continued reference to FIG. 3, cutting mechanism 250 is disposed on jaw housing 214 of jaw member 210. More particularly, cutting mechanism 250 is positioned on an external periphery of jaw member 210 opposite sealing surface 212 and towards a distal end of jaw member 210. Although shown disposed on jaw member 210, cutting mechanism 250 may alternatively be disposed on jaw member 220 in a similar fashion. Cutting mechanism 250 includes a blade track 268 extending longitudinally therealong, a blade protector 266 positioned at a distal end 264 thereof, e.g., at a distal end of blade track 268, and a stop member 260 positioned at a proximal end 262 thereof, e.g., at a proximal end of blade track 268. A cutting blade 270 is engaged within blade track 268 such that cutting blade 270 is longitudinally translatable along blade track 268 from distal end 264 to proximal end 262 thereof.

Blade track 268 may be configured to reduce splaying of cutting blade 270 upon translation of cutting blade 270 therethrough. For example, blade track 268 may define a specific configuration shaped complementarily to a base portion (not shown) of cutting blade 270 such that the base portion (not shown) of cutting blade 270 translates consistently through the complementary-shaped blade track 268.

Cutting blade 270 may be biased, e.g., spring biased, toward distal end 264 of cutting mechanism 250 such that, in an at-rest position, cutting blade 270 is disposed within blade protector 266. In other words, in the at-rest position, blade protector 266 substantially surrounds cutting blade 270 such that cutting blade 270 is not exposed. Accordingly, in the at-rest position, end effector assembly 200 may be maneuvered without the risk of accidental cutting, tearing, and/or catching tissue with cutting blade 270.

A trigger 70 (see FIG. 1), or a moveable switch (not shown) may be positioned on housing 20 of forceps 10 (FIG. 1) and operably coupled to cutting mechanism 250 and may be provided for selectively translating cutting blade 270 along blade track 268. Thus, upon actuation of trigger 70 (FIG. 1), cutting blade 270 may be translated proximally "P" from the distally-biased position within blade protector 266 to expose cutting blade 270. The exposed cutting blade 270 may be translated proximally along blade track 268 to the proximal end 262 of cutting mechanism 250. Stop member 260 is configured to prevent cutting blade 270 from further proximal translation once cutting blade 270 reaches proximal end 262 of cutting mechanism 250. Upon release of trigger 70 (FIG. 1), cutting blade 270 translates distally along blade track 268 under the bias, e.g., spring bias, to the at-rest position within blade protector 266.

In operation, end effector assembly 200 may be used to grasp and seal tissue, e.g., a vessel, disposed within the sealing area "S" defined between sealing plates 212, 222 of jaw members 210, 220, respectively, as mentioned above. During the manipulation of end effector 200, e.g., during positioning and/or approximation of jaw members 210, 220, or during tissue sealing, cutting blade 270 is disposed within blade protector 266, i.e., cutting blade 270 is unexposed, such that, as mentioned above, cutting blade 270 is prevented from accidentally cutting tissue. When tissue sealing is complete, cutting mechanism 250 may be used to sever, or divide the sealed vessel, or other tissue. To divide tissue, end effector assembly 200 is positioned such that tissue to be divided is disposed within cutting mechanism 250 between blade protector 266, i.e., the distal end 264 of cutting mechanism 250, and stop member 260, i.e., the proximal end 262 of cutting mechanism 250.

With tissue positioned within cutting mechanism 250, cutting blade 270 may be translated proximally along blade track 268, e.g., by actuation of a trigger 70. As cutting blade 270 is translated proximally in the direction of arrow "P," tissue disposed within cutting mechanism 250 is severed by the proximally-facing (and proximally translating) cutting blade 270. Cutting blade 270 is translated further proximally to completely divide tissue until cutting blade 270 contacts stop member 260.

Stop member 260 may help retain tougher or thicker tissue in position as cutting blade 270 is translated therethrough. More specifically, the positioning of stop member 260 inhibits proximal movement, or "pushing" of tissue by cutting blade 270, thereby facilitating translation of cutting blade 270 through tissue.

Once tissue has been completely severed, or divided, the operator may release trigger 70 to permit cutting blade 270 to translate distally to the unexposed, at-rest position within blade protector 266. End effector assembly 200 may then be manipulated, e.g., removed from the surgical site, without the risk of accidentally cutting tissue.

Figure 4:
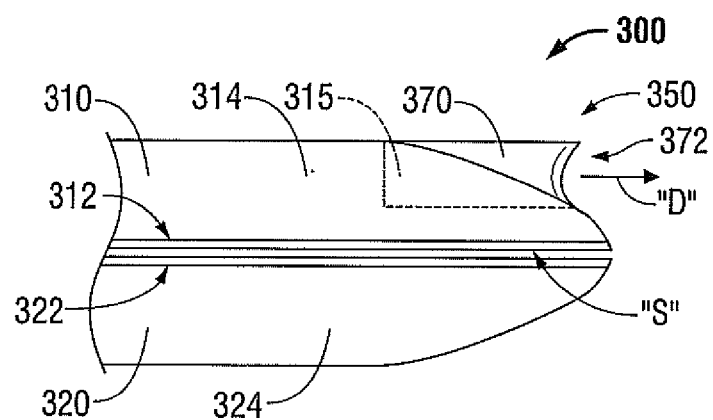
FIG. 4 is a side view of another embodiment of an end effector assembly for use with the forceps of FIG. 1.
Figure 5:
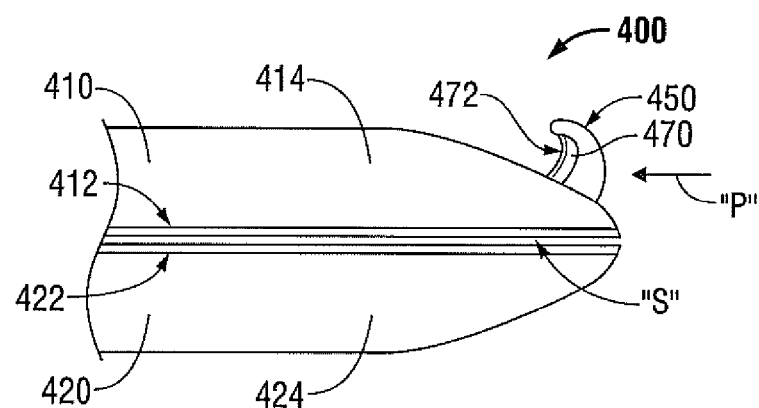
FIG. 5 is a side view of still another embodiment of an end effector assembly for use with the forceps of FIG. 1.

Referring now to FIGS. 4 and 5, other embodiments of an end effector assembly for sealing and/or cutting tissue are shown. As shown in FIG. 4, end effector assembly 300 includes first and second jaw members 310, 320 including jaw housings 314, 324, respectively, and opposing sealing surfaces 312, 322, respectively. Similarly with respect to FIG. 5, end effector assembly 400 includes first and second jaw members 410, 420 each including a jaw housing 414, 424, respectively, and a respective opposed sealing surface 412, 422.

As in the previous embodiments, each pair of jaw members, e.g., jaw members 310, 320 of end effector assembly 300 (FIG. 4) and jaw member 410, 420 of end effector assembly 400 (FIG. 5), are moveable with respect to each other between a spaced-apart position and an approximated position for grasping tissue therebetween. With tissue grasped between sealing surfaces 312, 322 or 412, 422, i.e., with tissue disposed within a sealing area "S," electrosurgical energy may be conducted to sealing surfaces 312 and 322 or 412 and 422 and through tissue to effect a tissue seal.

End effector assemblies 300, 400 each include an externally disposed cutting mechanism 350, 450, respectively, positioned thereon. More specifically, cutting mechanism 350 is disposed on jaw housing 314 of jaw member 310 opposite sealing surface 312 and is positioned toward a distal end thereof. Similarly, cutting mechanism 450 is disposed on jaw housing 414 of jaw member 410 opposite sealing surface 412 and is positioned toward a distal end thereof. Cutting mechanisms 350, 450 may be disposed on second jaw members 320, 420, respectively, rather than first jaw members 310, 320, in a similar fashion, or on both jaw members 310 and 320, 410 and 420.

With reference to FIG. 4, cutting mechanism 350 of end effector assembly 300 includes a cutting blade 370 extending distally from jaw housing 314 of jaw member 310. Cutting blade 370 includes an arcuate, distally facing cutting surface 372, although other configurations are contemplated. Cutting blade 370 may be selectively extendable from within a cavity 315 defined in jaw housing 314 from a retracted, or unexposed position (not shown) to an extended position (see FIG. 4). Thus, in the retracted position, the risk of accidentally cutting tissue during manipulation of end effector assembly 300 is greatly reduced.

In operation, cutting mechanism 350 may be used to dissect, or cut tissue. More particularly, end effector assembly 300 may be translated distally in the direction of arrow "D" (with cutting blade 370 in the extended position) with respect to tissue such that cutting surface 372 of cutting blade 370 is advanced into tissue, thereby cutting tissue.

With reference to FIG. 5, cutting mechanism 450 of end effector assembly 400 includes a blade holder 470 fixedly retaining a proximally-facing cutting blade 472 therein. Blade holder 470 protects cutting blade 472 during distal translation of end effector assembly 400 through tissue. In other words, as end effector assembly 400 is translated distally, tissue and/or other material in the path of end effector assembly 400 is pushed aside, and not severed, by the dull distal surface of blade holder 470. Further, the configuration of blade holder 470 prevents cutting blade 472 from becoming damaged during insertion and/or manipulation of end effector assembly 400.

In operation, when it is desired to cut tissue, end effector assembly 400 is positioned distally of tissue to be cut such that, when end effector assembly 400 is translated proximally in the direction of arrow "P" with respect to tissue, cutting blade 472 is advanced into tissue, thereby cutting tissue.

Figure 6:
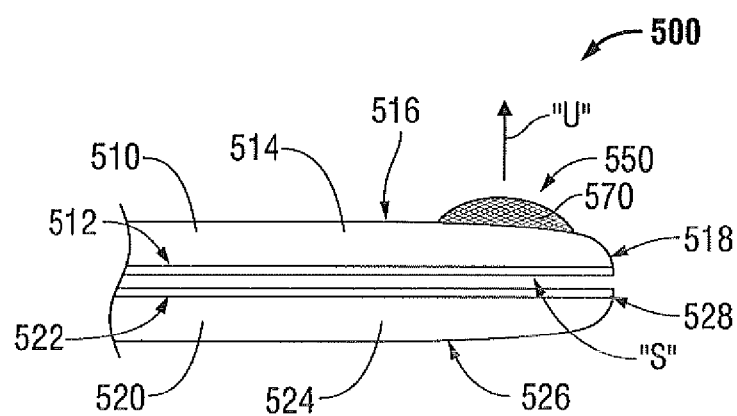
FIG. 6 is a side view of yet another embodiment of an end effector assembly for use with the forceps of FIG. 1.

With reference now to FIG. 6, end effector assembly 500 is shown including first and second jaw member 510, 520, respectively. Jaw members 510, 520 are moveable with respect to one another between a spaced-apart position and an approximated position for grasping tissue therebetween.

Each jaw member 510, 520 also includes an opposed electrically conductive sealing surface 512, 522, respectively, and a respective jaw housing 514, 524 defining an external top surface 516, 526, respectively, and a respective distal tip 518, 528. Sealing surfaces 512, 522 define a sealing area "S" therebetween and are adapted to connect to a source of electrosurgical energy for conducting electrosurgical energy to sealing surfaces 512, 522 and through tissue to effect a tissue seal.

Jaw housing 514 includes a cutting mechanism 550 disposed thereon and extending from external top surface 516 of jaw housing 514. Cutting mechanism 550 includes a dissecting, or cutting electrode 570. More specifically, dissecting electrode 570 extends normally from external top surface 516 of jaw housing 514 with respect to the longitudinal axis "A" (FIG. 1) extending through end effector assembly 500. Dissecting electrode 570 may be electrically coupled, independently of sealing surfaces 512, 522, to a source of electrosurgical energy for energizing dissecting electrode 570. Dissecting electrode 570 may be configured as a monopolar or a bipolar electrode.

A switch 90 (see FIG. 1), positioned on housing 20 of forceps 10 (FIG. 1) and operably coupled to end effector assembly 500 may be provided for transitioning end effector assembly 500 between an "off" mode, a "sealing" mode, and a "dissecting" mode. More specifically, when switch 90 (FIG. 1) is disposed in the "off" position, sealing surfaces 512, 522 and dissecting electrode 570 are deactivated, i.e., electrosurgical energy is not conducted to sealing surfaces 512, 522 or to dissecting electrode 570. In the "sealing" mode, or position, electrosurgical energy is supplied to sealing surfaces 512, 522 to effect a tissue seal, while dissecting electrode 570 remains deactivated. In the "dissecting" mode, sealing surfaces 512, 522 are deactivated and dissecting electrode 570 is activated, i.e., electrosurgical energy is supplied to dissecting electrode 570, for dissecting tissue.

In operation, as in the previous embodiments, sealing surfaces 512, 522 of jaw members 510, 520, respectively, may be approximated to grasp and seal tissue when end effector assembly is operating in the sealing mode.

In the dissecting mode, dissecting electrode 570 is activated i.e., supplied with electrosurgical energy, such that, upon translation of end effector assembly 500 with respect to tissue in the direction of arrow "U," dissecting electrode 570 is advanced into tissue to electrically dissect, or cut tissue. As can be appreciated, the positioning of dissecting electrode 570 atop jaw housing 514 allows end effector assembly 500 to be translated normally with respect to the longitudinal axis of end effector assembly 500, e.g., in the direction of arrow "U," during dissection of tissue. In such a configuration, jaw members 510, 520 are already aligned for grasping and sealing tissue during the dissection of tissue. Thus, a user need not rotate end effector assembly 500 upon reaching a portion of tissue to be grasped and/or sealed.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A forceps, comprising:
an end effector assembly including:
a pair of jaw members disposed in opposing relation relative to one another, at least one jaw member moveable relative to the other between a spaced-apart position and an approximated position for grasping tissue therebetween, each jaw member including a jaw housing and an opposed electrically conductive sealing surface, the opposed sealing surfaces cooperating to define a sealing plane therebetween in the approximated position; and
a cutting mechanism disposed on the jaw housing of one of the jaw members and fixed in relation relative to the jaw housing, the cutting mechanism spaced-apart from the sealing plane and disposed in non-intersecting relation relative to the sealing plane, the cutting mechanism including a cutting blade and a blade holder, the blade holder positioned distally of the cutting blade and configured to prevent the cutting blade from cutting tissue when the end effector assembly is translated distally with respect to tissue, the cutting blade having a proximally-facing cutting edge extending from the jaw housing such that the cutting blade cuts tissue externally-positioned relative to the jaw members upon proximal translation of the cutting mechanism with respect to tissue.

2. A surgical instrument, comprising:
an end effector assembly including:
a pair of jaw members disposed in opposing relation relative to one another, at least one jaw member moveable relative to the other between a spaced-apart position and an approximated position for grasping tissue therebetween, each jaw member including a jaw housing and an opposed electrically conductive sealing surface, the opposed sealing surfaces cooperating to define a sealing plane therebetween in the approximated position; and
a cutting mechanism disposed on an external periphery of the jaw housing of one of the jaw members, the cutting mechanism spaced-apart from the sealing plane and disposed in non-intersecting relation relative to the sealing plane, the cutting mechanism including:
a blade track extending longitudinally therealong, the blade track having a distal end and a proximal end; and
a cutting blade engaged within the blade track and proximally translatable with respect to the blade track from the distal end to the proximal end thereof to cut tissue disposed therebetween.

3. The forceps according to claim 2, wherein the cutting blade is biased toward the distal end of the blade track.

4. The forceps according to claim 2, wherein the distal end of the blade track is nested within a blade protector such that the cutting blade is disposed within the blade protector when the cutting blade is positioned at the distal end of the blade track.

5. The forceps according to claim 2, wherein a stop member is positioned at the proximal end of the blade track.

* * * * *